(12) United States Patent
Ranganathan

(10) Patent No.: US 9,072,768 B2
(45) Date of Patent: Jul. 7, 2015

(54) COMPOSITION AND METHOD FOR INCREASING EFFECTIVENESS OF RADIATION OR CHEMOTHERAPY

(71) Applicant: Kibow Biotech, Inc., Newtown Square, PA (US)

(72) Inventor: Natarajan Ranganathan, Broomall, PA (US)

(73) Assignee: Kibow Biotech, Inc., Newtown Square, PA (US)

(*) Notice: Subject to any disclaimer, the term of this patent is extended or adjusted under 35 U.S.C. 154(b) by 0 days.

(21) Appl. No.: 13/746,418

(22) Filed: Jan. 22, 2013

(65) Prior Publication Data
US 2014/0205572 A1  Jul. 24, 2014

(51) Int. Cl.
| | |
|---|---|
| *A61K 36/185* | (2006.01) |
| *A61K 35/74* | (2006.01) |
| *A61K 35/744* | (2015.01) |
| *A61K 35/745* | (2015.01) |
| *A61K 35/747* | (2015.01) |
| *A61K 36/77* | (2006.01) |
| *A61K 36/07* | (2006.01) |
| *A61K 45/06* | (2006.01) |

(52) U.S. Cl.
CPC .............. *A61K 35/744* (2013.01); *A61K 35/745* (2013.01); *A61K 35/747* (2013.01); *A61K 36/77* (2013.01); *A61K 36/07* (2013.01); *A61K 45/06* (2013.01)

(58) Field of Classification Search
CPC ............ A61K 2300/00; A61K 35/747; A61K 35/745; A61K 35/741; A61K 36/06
USPC ........................................ 424/93.3
See application file for complete search history.

(56) References Cited

U.S. PATENT DOCUMENTS

2009/0252709 A1* 10/2009 Nose et al. .................. 424/93.4
2011/0206721 A1   8/2011 Nair ....................... 424/195.15

OTHER PUBLICATIONS

Gutierrez, Use lychee fruit to boost your endurance and workouts: Research, Natural News, Sunday, Jun. 2, 2013, available online at: www.naturalnews.com/040593_lychee_fruit_exercise_endurance.html.*
Rockwell Nutrition, AHCC Booklet, Created Nov. 30, 2001, Available online at: www.rockwellnutrition.com/assets/images/docs/AHCCbrochure.pdf.*
Jong, S.C. and Birmingham, J.M. "Medicinal and Therapeutic Value of the Shiitake Mushroom" Advances in Applied Microbiology 1993 39:153-184.
Kanlayavattanakul et al. "Biological Activity Assessment and Phenolic Compounds Characterization from the Fruit Pericarp of *Litchi chinensis* for Cosmetic Applications" Pharmaceutical Biology 2012 50(11):1384-1390.
Kawaguchi, Yusai "Improved Survival of Patients with Gastric Cancer or Colon Cancer when Treated with Active Hexose Correlated Compound (AHCC): Effect of AHCC on Digestive System Cancer" Natural Medicine Journal 2009 1:1-6.
Liong, Min-Tze "Roles of Probiotics and Prebiotics in Colon Cancer Prevention: Postulated Mechanisms and In-vivo Evidence" International Journal of Molecular Sciences 2008 9:854-863.
Liu, C. and Pan T. "In Vitro Effects of Lactic Acid Bacteria on Cancer Cell Viability and Antioxidant Activity" Journal of Food and Drug Analysis 2010 18:77-86.
Zhao et al. "Identification of the Major Flavanoids from Pericarp Tissues of Lychee Fruit in Relation to their Antioxidant Activities" Food Chemistry 2006 98:539-44.

* cited by examiner

*Primary Examiner* — Karen Cochrane Carlson
*Assistant Examiner* — Jennifer M. H. Tichy
(74) *Attorney, Agent, or Firm* — Licata & Tyrrell P.C.

(57) ABSTRACT

This invention is a composition containing prebiotics, *Lentinula edodes* mycelia extract, and *Litchi chinensis* fruit polyphenol and use of the same in increasing the effectiveness of radiation or chemotherapy and in the prevention, mitigation and/or treatment of colorectal neoplasia.

10 Claims, No Drawings

COMPOSITION AND METHOD FOR INCREASING EFFECTIVENESS OF RADIATION OR CHEMOTHERAPY

BACKGROUND OF THE INVENTION

Worldwide, colorectal cancer is the third most common cause of death in cancer and approximately one million individuals are diagnosed each year. Despite optimal surgical treatment and modern adjuvant chemotherapy, half of patients have recurrences and ultimately die within 5 years from diagnosis. The most important prognostic factors are presence of lymph node or distant metastases, being found in about 50% of all cases. Patients with locoregional lymph node metastases, Duke's C/stage III, have about 60% 5-year survival after surgery, and when distant metastases are present, the 5-year survival rate is less than 10%. The established, adjuvant treatment in stage III patients is 5-Fluorouracil (5-FU)-based chemotherapy, improving absolute 5-year survival by approximately 10%. There is no evidence for a statistically significant survival benefit for chemotherapy in Duke's B/Stage II patients. However, 20% of patients being classified as lymph node-negative will suffer from recurrent disease. Some of these patients are likely to be understaged, since it is widely accepted that accurate staging of colon cancer is difficult and heavily dependent on the number of lymph nodes analyzed by the pathologist. The sentinel node, originally defined in penile carcinoma, is the first lymph node to receive lymphatic drainage from a tumor. Sentinel node detection and analysis has recently been applied in colon cancer, improving staging considerably.

The immune system often appears informed about tumors, as shown by an accumulation of immune cells at tumor sites, which correlates with improved prognosis. Two different models for the immune response to tumors have been proposed: the concept of immunosurveillance and the danger model. According to the immunosurveillance hypothesis, tumors expressing antigens are regarded as "non-self" by the immune system, and a major function of the immune system is to survey the body for the development of malignancy and to eliminate tumor cells as they arise (Burnet (1970) *Prog. Exp. Tumor Res.* 13:1-27). To detect "danger," the immune system uses professional antigen-presenting cells (APC) as sentinels of tissue damage. In the presence of danger signals, APC (e.g., dendritic cells, activated macrophages, and B cells) stimulate the T cell response. The danger model proposes that cancer cells do not appear dangerous to the immune system, so that the response of T cells to tumors is not initiated (Fuchs & Matzinger (1996) *Semin. Immunol.* 8:271-280).

Natural killer (NK) cells of the innate immune system also play an important role in immune surveillance of tumors (Smyth, et al. (2001) *Nat. Immunol.* 2:293-99). NK cells kill MHC class I-deficient cells, a phenomenon that is part of the "missing self" hypothesis (Watzl & Long (2000) *Nat. Med.* 6:867-8; Pardoll (2001) *Science* 294:534-6). The activity of NK cells is controlled by a balance of positive and negative signals. Engagement of inhibitory receptors by MHC class I molecules blocks activation signals. Two families of inhibitory receptors have been identified in humans: the immunoglobulin-like killer cell inhibitory receptors and the lectin-like CD94-NKG2 receptors. Stimulatory receptors include receptors (e.g., CD16, CD94-NKG2C, natural cytotoxicity receptors) that are supposed to bind to constitutively expressed ligands (Moretta, et al. (2000) *Immunol. Today* 21:228-34) and NKG2d receptors, which bind to molecules that are induced by cellular stress (Cerwenka, et al. (2000) *Immunity* 12:721-7; Bauer, et al. (1999) *Science* 285:727-9; Wu, et al. (1999) *Science* 285:730-2). Ligands for NKG2d receptors are the MHC class I chain-related (MIC) glycoproteins MICA and MICB in humans and the minor histocompatibility antigen H60 and the retinoic acid early inducible (Rae-1) family in mice.

Additional cells of the innate immune system involved in immunity against tumors are macrophages and neutrophils (Lollini & Formi (1999) *Immunol. Today* 20:347-350; Di Carlo, et al. (2001) *Blood* 97:339-45; Elgert, et al. (1998) *J. Leukoc. Biol.* 65:275-90; Bonnotte, et al. (2001) *J. Immunol.* 167:5077-83). These cells can reject tumors by direct killing of the tumor cells, by destruction of tumor vessels and matrix, and by inhibition of angiogenesis. Moreover, they display tumor antigens and can stimulate other immune cells such as CTL, NK cells, or APC. In contrast, inflammatory cells may also contribute to tumor progression by production of tumor growth factors and stimulation of angiogenesis (Lin, eta l. (2001) *J. Exp. Med.* 193:727-40). Macrophages and neutrophils are recruited to the tumor site by expression of adhesion molecules on endothelial cells and by chemotactic proteins.

In the adjuvant setting, tumor immunotherapy offers an appealing alternative to traditional cytostatics. One strategy has been to expand and activate NK cells in vitro without specific antigen by culturing with IL-2 followed by infusion of large numbers of these NK cells back into patients alone or with high doses of IL-2. This approach, or administration of high doses of IL-2 to expand and activate NK cells entirely in vivo, has yielded antitumor activity and remission in a subset of patients (Rosenberg, et al. (1993) *J. Natl. Cancer Inst.* 85:622). However, life-threatening toxicity often develops, largely due to the release of tumor necrosis factor (TNF) from activated NK cells. Other attempts to stimulate the innate specific T cell immunity have been done by different types of vaccines. Promising results from animal studies entailed a study in which autologous tumor cells and an adjuvant immunomodulating agent, *Bacillus* Calmette-Guerin (BCG) was given in combination several times to 98 patients with colorectal cancer in a prospectively randomized study (Hoover, et al. (1993) *J. Clin. Oncol.* 11:390-9). No statistically significant differences were detected in survival; however, a small decrease in recurrence rate in stage II colon cancer patients was observed. Further studies were done but no statistical clinical benefit in disease-free interval or survival could be seen, not even when combined with 5-FU and Leucovorin.

A synbiotic containing *Lactobacillus rhamnoses* GG and *Bifidobacterium lactis* Bb12 and oligofructose-enriched inulin has been suggested to alter certain colorectal cancer intermediate biomarkers, and reduce colorectal proliferation (Liong ((2008) *Int. J. Mol. Sci.* 9:854-863). Further, heat killed cells of *L. plantarum, L. delbrueckii* ssp. bulgaricus, *L. salivarius* ssp. salivarius, *B. longum* and *L. plantarum* have been shown to reduce the viability of HT-29 colon cancer cells, whereas *L. plantarum, L. acidophilus, L. salivarius* ssp. salivarius, *B. longum* and *B. infantis* have been shown to reduce the viability of Caco-2 colon cancer cells (Liu & Pan ((2010) *J. Food Drug Analysis.* 18:77-86).

US 2011/0206721 teaches a dietary supplement provided in powder form, which includes a mixture of mushrooms grown in fermented soy and curcumin, for use as a chemopreventive in colon cancer. The inclusion of an edible mushroom such as *Lentinus edodes* or mushroom ingredient thereof, or lychee powder is also suggested.

SUMMARY OF THE INVENTION

This invention is composition composed of a *Streptococcus, Bifidobacterium*, at least one *Lactobacillus, Lentinula* edodes mycelia extract, and *Litchi chinensis* fruit polyphenol. In some embodiments, the *Streptococcus* is *S. thermophilus*, the *Bifidobacterium* is *B. lactis*, the *Lactobacillus* is one or more of *L. acidophilus, L. planatarum*, or *L. rhamnosus*. In other embodiments, the composition further includes a prebiotic and/or at least one excipient and can take the form of a food product, dietary supplement, comestible medical food, pharmaceutical product, or nutraceutical product. Methods for using the composition of this invention to increase the effectiveness of radiation or chemotherapy and prevent, mitigate or treat colorectal neoplasia are also provided.

DETAILED DESCRIPTION OF THE INVENTION

A novel cancer immunotherapy has now been developed. This immunotherapy is a combination of probiotic bacteria including a *Streptococcus*, a *Bifidobacterium*, and at least one *Lactobacillus*, with *Lentinula edodes* mycelia extract, and *Litchi chinensis* fruit polyphenol and use of the same to enhance immunity, increase the effectiveness of radiation or chemotherapy, and in the prevention and treatment of colorectal neoplasia.

A probiotic bacterium of this invention refers to a mono or mixed culture of live or freeze-dried microorganisms which, when administered to man or animal, beneficially affects the host. Probiotic bacteria of this invention are selected for their ability to exert a beneficial effect on the host, survive transit through the intestinal tract, to adhere to intestinal epithelial cell lining, and enhance immunity. Furthermore, a probiotic component should have a good shelf-life. Compositions of this invention generally contain a large number of viable cells at the time of consumption, and are non-pathogenic and non-toxic. Examples of probiotic components include, but are not limited to, *Bifidobacterium* spp. (e.g., bifidum, longum, infantis), *Lactobacillus* spp. (e.g., bulgaricus, acidophilus, lactis, helveticus, casei, plantarum, reuteri, delbrueckii, rhamnosus, johnsonii), *Streptococcus* spp. (e.g., thermophilus, diacetilactis, cremoris, durans, faecalis), *Saccharomyces* spp. (e.g., pombe, boulardii), *Leuconostoc* spp. (e.g., citrovorum, dextranicum) and *Bacillus* sp. (e.g., pasteurii). In one embodiment, the probiotic component is composed of a *Streptococcus*, a *Bifidobacterium*, and at least one *Lactobacillus*. In some embodiments, the probiotic component of this invention is composed of a *Streptococcus*, a *Bifidobacterium*, and at least two *Lactobacillus* species. In other embodiments, the probiotic component of this invention is composed of a *Streptococcus*, a *Bifidobacterium*, and at least three *Lactobacillus* species. In specific embodiments, the probiotic component of this invention is composed of *S. thermophilus, B. lactis, L. acidophilus, L. planatarum*, and *L. rhamnosus*.

Microorganisms also useful in the invention are those that have the ability, either through natural selection or by genetic manipulation, to catabolize various nitrogenous compounds (e.g., urea, creatinine, uric acid and ammonia) by expressing or overexpressing one or more cognate catabolic enzymes. Exemplary microorganisms are those having an elevated level of urease or creatininase secretion.

A microorganism exhibiting elevated levels of catabolic enzyme secretion can be selected or trained by exposing a selected microorganism on increasing amounts of the metabolite of interest (e.g., urea, creatinine, uric acid and ammonia). For example, it has been found that a standard strain of *S. thermophiles* can be trained to express elevated levels of urease by sequential passage of the strain on increasing amounts of urea, e.g., a single colony growing on 0.5% urea is selected and applied to medium containing 1.0% urea, a single colony growing on 1.0% urea is selected and applied to medium containing 2.0% urea, etc. Using such a method, a *S. thermophiles* strain having the ability to grow on 5% urea was isolated. This strain proliferated in artificial intestinal fluid (AIF, US Pharmacopeia) in the pH range of 5.5 to 7.5, characteristic of the colon environment; used urea as a sole nitrogen source; and catabolized urea in the presence of other nitrogen sources. It was found that urea hydrolysis was growth- and pH-dependent and that urea concentrations could be reduced by this strain from 300 mg/dL to 20 mg/dL within 24 hours at pH 6.3 when inoculated in AIF at an initial density of $10^9$ cfu/mL. Moreover, this strain survived 3 hours in acidic pH 3.0 with only a one-log loss in cfu and was able to pass through bile. In addition, this strain did not appear to exhibit any resistance to eight commonly used antibiotics. Therefore, these data indicate that a specifically selected or trained bacterial isolate can be used as a urea-targeted component in a product of the present invention.

Elevated levels of secretion can also be obtained by overexpressing the gene of interest (e.g., via multiple copies or a promoter driving high levels of expression) in a prokaryotic microorganism of interest such as *Bifidobacterium, Lactobacillus, Streptococcus, Leuconostoc* or *Bacillus*, or a eukaryotic microorganism such as *Saccharomyces*. The gene of interest can be under the regulatory control of an inducible or constitutive promoter. Promoters for use in recombinant prokaryotic expression vectors are well-established in the art and can include the beta-lactamase (penicillinase) and lactose promoter systems (Chang, et al. (1978) *Nature* 275:615; Goeddel, et al. (1979), *Nature* 281:544), a tryptophan (trp) promoter system (Goeddel, et al. (1980) *Nucleic Acids Res.* 8:4057; EP 36,776) and the tac promoter (De Boer, et al. (1983) *Proc. Natl. Acad. Sci. USA* 80:21). While these are commonly used promoters which are commercially available, one of skill in the art can appreciate that any other suitable microbial promoter can be used as well. Nucleic acid sequences encoding suitable prokaryotic promoters have been published thereby enabling one of skill in the art to readily isolate these promoters (e.g., by standard cloning or PCR methodologies) for cloning into plasmid or viral vectors (Siebenlist, et al. (1980) *Cell* 20:269). The promoter and Shine-Dalgarno sequence (for prokaryotic host expression) are operably-linked to the DNA encoding the gene of interest, i.e., they are positioned so as to promote transcription of the messenger RNA from the DNA, and subsequently introduced into a suitable host cell.

Eukaryotic microbes such as yeast cultures can also be transformed with suitable protein-encoding vectors. See e.g., U.S. Pat. No. 4,745,057. *Saccharomyces cerevisiae* is the most commonly used among lower eukaryotic host microorganisms, although a number of other strains are commonly available. Yeast vectors can contain an origin of replication from the micron yeast plasmid or an autonomously replicating sequence (ARS), a promoter, DNA encoding the desired protein, sequences for polyadenylation and transcription termination, and a gene encoding for a selectable marker. An exemplary plasmid is YRp7, (Stinchcomb, et al. (1979) *Nature* 282:39; Kingsman, et al. (1979) *Gene* 7:141; Tschemper, et al. (1980) *Gene* 10:157). This plasmid contains the trp1 gene, which provides a selection marker for a mutant strain of yeast lacking the ability to grow in tryptophan, for example ATCC No. 44076 or PEP4-1 (Jones (1977) *Genetics* 85:12). The presence of the trp1 lesion in the yeast host cell genome then provides an effective environment for detecting transformation by growth in the absence of tryptophan.

Suitable promoting sequences in yeast vectors include the promoters for metallothionein, 3-phosphoglycerate kinase (Hitzeman, et al. (1980) *J. Biol. Chem.* 255:2073) or other glycolytic enzymes (Hess, et al. (1968) *J. Adv. Enzyme Reg.* 7:149; Holland, et al. (1978) *Biochemistry* 17:4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are commercially available and further described in EP 73,657.

As will be understood by those of skill in the art, expression vectors containing polynucleotides that encode a degradative enzyme of interest, e.g., a urease or creatininase, can be designed to contain signal sequences which direct secretion of enzyme of interest through a prokaryotic or eukaryotic cell membrane. Such signal sequences are well-established in the art and can be taken from other enzymes/proteins known to be secreted into the extracellular environment.

Transforming the microorganisms as defined herein, is a process by which exogenous DNA is introduced into and changes a recipient cell. It can occur under natural or artificial conditions using various methods well-known in the art. Transformation can rely on any known method for the insertion of foreign nucleic acid sequences into a prokaryotic or eukaryotic host cell. The method is selected based on the type of host cell being transformed and can include, but is not limited to, viral infection, electroporation, heat shock, lipofection, and particle bombardment. Such "transformed" cells include stably-transformed cells in which the inserted DNA is capable of replication either as an autonomously replicating plasmid or as part of the host chromosome. This also includes cells which transiently express the inserted DNA or RNA for limited periods of time.

As will be appreciated by the skilled artisan, a microorganism can also be exposed to a mutagen to cause changes in the genetic structure of the organism so that it expresses elevated levels of a catabolic enzyme of interest.

Transformed or mutagenized strains are subsequently selected for the ability to grow in the presence of the metabolite which is degraded by the catabolic enzyme of interest. By way of example, a strain transformed with nucleic acid sequences encoding a urease is selected for high levels of urease secretion by growing said strain on high levels of urea. Levels of urease secretion can also be detected using standard enzymatic assays. As disclosed herein, the strain can be sequentially subcultured on increasing levels of urea to further enhance urease secretion. One embodiment of the present invention provides a urease-secreting strain of *B. pasteurii*, *S. thermophilus* or *S. pombe*. In another embodiment, a urease-secreting strain is at least one of the microorganisms of a probiotic component composed of at least two or at least three microorganisms. In a further embodiment, a urease-secreting strain is at least two of the microorganisms of a probiotic component composed of at least three microorganisms.

The probiotics according to the invention can be obtained by fermentation and can be stored after fermentation and before addition to the composition of this invention for a time and at a temperature that prevents substantial loss of probiotic colony forming units (cfu). For example, the probiotic component can be fermented until a final concentration of $10^6$ to $5 \times 10^{10}$, or $10^7$ to $10^{10}$, or $10^8$ to $10^9$ cfu per mL of fermented medium is achieved. In certain embodiments, the probiotic component of the composition of this includes at least 20 billion cfu bacteria.

Each organism of the probiotic component can be 10, 15, 20, 30, 40, 50, 60, 70, 80, or 90% of the probiotic component, wherein the total of all microorganisms is 100%. An exemplary probiotic component is composed of about 25% *S. thermophilus*, about 12.5% *B. lactis*, about 25% *L. acidophilus*, about 25% *L. planatarum* and about 12.5% *L. rhamnosus* (e.g., a ratio of approximately 2:1:2:2:1, respectively). The probiotic component is included at a concentration of $10^8$ cfu/mL, $10^9$ cfu/mL, $10^{10}$ cfu/mL, $10^{11}$ cfu/mL, or $10^{12}$ cfu/mL when added as a liquid or $10^8$ cfu/g, $10^9$ cfu/g, $10^{10}$ cfu/g, $10^{11}$ cfu/g, or $10^{12}$ cfu/g when added as a freeze-dried powder.

In one embodiment, the probiotic component is about 20% to about 70% of the total composition weight. In particular embodiments, the probiotic component is about 50% of the total composition weight.

Also included in the composition of this invention is an extract from the mycelia of *Lentinula edodes* (shiitake mushroom). It is believed that the *L. edodes* mycelia extract beneficially affects the host by selectively stimulating the growth and/or activity of one or more non-pathogenic bacteria in the colon. *L. edodes* mycelia extract can be obtained by culturing the mycelia of *L. edodes* alone or in combination with other basidiomycetes (mushroom root threads) for a period of 45-60 days medium containing rice bran. After culturing is complete, the mycelia are subjected to enzyme reaction, sterilization, concentration and freeze drying. The resulting product is composed of about 70% oligosaccharides, including β-glucan and acetylated, low molecular weight (5000 daltons) α-glucan (~20%). Alternatively, *L. edodes* mycelia extract can be obtained from commercial sources. For example, Active Hexose Correlated Compounds (AHCC; Quality of Life Labs, Purchase, N.Y.) is an alpha-glucan rich nutritional extract produced from the mycelia of shiitake, which has been suggested to improve the survival of patients with early state gastric cancer or colon cancer (Kawaguchi ((2009) *Nat. Med. J.* 1:1; Jong & Birmingham (1993) *Adv. Appl. Microbiol.* 39:153-184). The amount of *L. edodes* mycelia extract used in the composition of this invention is desirably in the range of 100 mg to 600 mg, or 200 to 500 mg, or more preferably 250 to 400 mg.

*Litchi chinensis* fruit (lychee fruit) polyphenol can be obtained by extracting phenolics from the lychee fruit pericarp (Zhao, et al. (2006) *Food Chem.* 98:539-44). For example, lychee pericarps are macerated in 70% ethanol and partitioned using n-hexane and ethyl acetate. The ethyl acetate fraction, which contains phenolic compounds such as quercetin, rosmarinic and gallic acids (Kanlayavattanakul, et al. (2012) *Pharm. Biol.* 50(11):1384-90), is retained and used as a dried product. Alternatively, lychee fruit polyphenol can be obtained commercially from any source or supplier. For example, OLIGONAL (Quality of Life Labs, Purchase, N.Y.) is a phenolic product from lychee fruit polyphenol containing catechin-type monomers and lower oligomers of proanthocyanidin. The amount of lychee fruit polyphenol used in the composition of this invention is desirably in the range of 50 mg to 200 mg, or 100 to 150 mg, or more preferably 100 mg.

In some embodiments, the composition of the invention further includes a prebiotic component. Prebiotic components of the present invention are considered to have anticarcinogenic, anti-microbial, hypolipidemic and glucose modulatory activities. They can also improve mineral absorption and balance. Furthermore, bacteria belonging to the *Bifidobacterium* and *Lactobacillus* families are stimulated by the presence of the prebiotic component and proliferate. Pharmacokinetically, the prebiotic components reach the colon largely intact. An exemplary prebiotic component includes, but is not limited to, an oligosaccharide such as fructo-oligosaccharide or inulin, isomaltose oligosaccharide, trans-galacto-oligosaccharide, xylo-oligosaccharide, or soy-oligosaccharide; a pyrodextrin such as arabinogalactan, lactilol, lactosucrose, or lactulose; or a fiber source such as oat gum, pea fiber, apple fiber, pectin, guar gum, psyllium husks, glucomannan or guar gum hydrolysate (BENEFIBER, Novartis Pharmaceuticals). In one embodiment, the prebiotic component is composed of at least one, at least two, or at least three non-digestive foods (e.g., oligosaccharides, pyrodextrins or a fiber source). In another embodiment, an oligosaccharide is at least one of the non-digestive foods of a prebiotic component composed of at least two or at least three non-digestive foods. In yet another embodiment, a fiber source is at least one of the non-digestive foods of a prebiotic component composed of at least two or at least three non-digestive foods. In a further embodiment, a fiber source is at least two of the non-digestive foods of a prebiotic component composed of at least three non-digestive foods. In a still further embodiment, the prebiotic component is composed of at least one of the following non-digestive foods of lactulose, psyllium husks and guar gum hydrolysate. In particular embodiments, the prebiotic component is psyllium husks.

In addition to containing probiotic components, *L. edodes* mycelia extract, and *L. chinensis* fruit polyphenol the product of the present invention can further contain various excipients, bulking agents, binders, sweeteners, flavors and/or additives. Optional excipients of the present composition include, without limitation, lubricants such as magnesium stearate or stearic acid, or talc; binders such as starch or sugars; fats, antioxidants, amino acids, proteins, nucleic acids, electrolytes, vitamins, derivatives thereof or combinations thereof. In one embodiment, an additive of the product is carob flour, for example, locust bean gum. In another embodiment, an additive is a mushroom extract from *Agaricus bisporus*. In particular embodiments, a product contains excipients such as magnesium stearate and/or stearic acid.

Further, to increase the palatability of a food product of this invention, it may be desirable to add flavors, sweetening agents, binders or bulking agents. Flavors which can optionally be added to the present compositions are those well-known in the art. Examples include, but are not limited to, synthetic flavor oils, and/or oils from plants leaves, flowers, fruits and so forth, and combinations thereof are useful. Examples of flavor oils include, but are not limited to, spearmint oil, peppermint oil, cinnamon oil, and oil of wintergreen (methylsalicylate). Also useful are artificial, natural or synthetic fruit flavors such as citrus oils including lemon, orange, grape, lime, and grapefruit, and fruit essences including apple, strawberry, cherry, pineapple and so forth. Sweetening agents can be selected from a wide range of materials such as water-soluble sweetening agents, water-soluble artificial sweeteners, and dipeptide-based sweeteners, including salts thereof and mixtures thereof, without limitation.

Binders can be selected from a wide range of materials such as hydroxypropylmethylcellulose, ethylcellulose, or other suitable cellulose derivatives, acrylic and methacrylic acid co-polymers, pharmaceutical glaze, gums (e.g., gum tragacanth), milk derivatives (e.g., whey), starches (e.g., corn starch) or gelatin, and derivatives, as well as other conventional binders well-known to persons skilled in the art. Examples of bulking substances include, but are not limited to, sugar, lactose, gelatin, starch, and silicon dioxide.

When the above-mentioned additives are included in the product of the present invention, they are generally less than 15% of the total product weight. In particular embodiments, they are less than 5 to 10% of the total product weight.

One example of a composition of the present invention contains a *Streptococcus, Bifidobacterium*, at least one *Lactobacillus, Lentinula edodes* mycelia extract, and *Litchi chinensis* fruit polyphenol. Another example of a composition of the present invention contains a *Streptococcus, Bifidobacterium*, at least one *Lactobacillus, Lentinula edodes* mycelia extract, *Litchi chinensis* fruit polyphenol, and a prebiotic. An exemplary composition of the invention includes *S. thermophilus, B. lactis, L. acidophilus, L. planatarum, L. rhamnosus, Lentinula edodes* mycelia extract, and *Litchi chinensis* fruit polyphenol. Another exemplary composition of this invention includes *S. thermophilus, B. lactis, L. acidophilus, L. planatarum, L. rhamnosus, Lentinula edodes* mycelia extract, *Litchi chinensis* fruit polyphenol, and a prebiotic such as an oligosaccharide, a pyrodextrin, or a fiber source.

Depending on whether the product is to be consumed by an adult human, child or animal (e.g., companion animal or livestock), it can be produced in various sizes and with various ingredients suitable for the intended recipient. Further, because the composition of the present invention is generally recognized as safe, they can be consumed one, two or three times daily or more. Repeated ingestion of the product of this invention will have a highly beneficial effect upon the intestinal microflora by localization and colonization in the large intestine of microbes known to promote a healthy intestinal microenvironment.

A composition of this invention can be in the form of a food product (e.g., a health bar, health drink, yogurt, dahi, ice cream, frozen yogurt or other frozen food product), dietary supplement, comestible medical food, pharmaceutical product, or nutraceutical product.

The ingestion of a composition of this invention provides both immune-enhancing and anti-carcinogenic activity. In this respect, the present composition can be administered alone or in combination with known chemotherapeutic or radiotherapeutic agents that are conventionally used in the treatment of cancer. When administered in combination with a chemotherapeutic or radiotherapeutic agent, the composition of this invention can increase the effectiveness of the chemotherapeutic or radiotherapeutic agent by enhancing, accentuating or promoting faster recovery. When administered alone, the composition of this invention can prevent, treat and/or mitigate cancer, in particular colorectal neoplasias.

The most common drug used for chemotherapy is of 5-fluoro-uracil (5FU). It is administrated in intravenous form. In addition, 5FU with an adjuvant, namely levamisole or leucovorin, has also been used in the treatment of colon cancer. Other drugs of use against colon cancer include, but are not limited to, Irinotecan (CPT-11), Oxaliplatine, Ralitrexed and Capecitabine.

As used herein, the term "treatment" or "treating" means any therapeutic intervention in a mammal, preferably a human or any other animal suffering from cancer, such that symptoms and/or tumor size and number are reduced. "Prevention" or "preventing" refers to prophylactic treatment causing the clinical symptoms not to develop, e.g., preventing a tumor from occurring and/or developing. "Mitigation" or "mitigating" means arresting the development of clinical symptoms, e.g., stopping or delaying tumor growth, or providing relief or regression of clinical symptoms, e.g., a decrease in abdominal pain, a decrease in diarrhea, or a decrease in constipation.

In accordance with this invention, a subject in need of treatment is administered an effective amount of a composition of this invention, to provide a measurable benefit such as enhanced recovery from radiation therapy or chemotherapy, or prevention, mitigation, or treatment of signs or symptoms of cancer. Subjects benefiting from the method of the invention include those having cancer (e.g., exhibiting signs or symptoms of cancer and, in some embodiments, receiving radiation therapy or chemotherapy) or those at risk of having cancer (e.g., a subject predisposed to cancer or recurrence of cancer), in particular a colorectal neoplasia.

Colorectal neoplasias encompass large intestine, bowel, colon and rectal neoplasias, including colorectal neoplasias that are non-angiogenin secreting and/or non-angiogenin-dependent. In one embodiment, target patients have undergone removal or ablation of a colorectal neoplasia and are determined to be predisposed to colorectal neoplasia recurrence, including patients having a known predisposition, particularly a genetic predisposition, due to familial history of colon cancer, especially in association with a known syndrome such as familial adenomatous polyposis or hereditary non-polyposis colon cancer.

The amount and dosage regimen of the composition of the invention to be administered is determined in the light of various relevant factors including the purpose of administration (e.g., prevention, mitigation or treatment), the age, sex and body weight of an individual subject, and/or the severity of the subject's symptoms. In this respect, the compositions of the invention can be administered under the supervision of a medical specialist, or may be self-administered.

What is claimed is:

1. A composition for increasing effectiveness of radiation or chemotherapy and/or treating colorectal neoplasia, said composition comprising a *Streptococcus, Bifidobacterium*, at least one *Lactobacillus*, sterilized *Lentinula edodes* mycelia extract, and *Litchi chinensis* fruit polyphenol extract, wherein the *Streptococcus, Bifidobacterium*, and at least one *Lactobacillus* are viable, wherein the *Streptococcus* is *Streptococcus thermophilus* selected for the ability to reduce urea concentrations from 300 mg/dL to 20 mg/dL within 24 hours at pH 6.3.

2. The composition of claim 1, wherein the *Bifidobacterium* comprises *B. lactis*.

3. The composition of claim 1, wherein the *Lactobacillus* consists of *L. acidophilus, L. planatarum*, or *L. rhamnosus*.

4. The composition of claim 1, wherein the *Lactobacillus* comprises *L. acidophilus, L. planatarum*, and *L. rhamnosus*.

5. The composition of claim 1, further comprising at least one prebiotic.

6. The composition of claim 1, further comprising at least one excipient.

7. The composition of claim 1, wherein the composition comprises a food product, dietary supplement, comestible medical food, pharmaceutical product, or nutraceutical product.

8. A composition consisting essentially of *Streptococcus thermophilus, Bifidobacterium lactis, Lactobacillus acidophilus, L. planatarum, L. rhamnosus*, sterilized *Lentinula edodes* mycelia extract, *Litchi chinensis* fruit polyphenol and a prebiotic, wherein the *Streptococcus thermophilus* is selected for the ability to reduce urea concentrations from 300 mg/dL to 20 mg/dL within 24 hours at pH 6.3.

9. A method for increasing the effectiveness of radiation or chemotherapy comprising administering to a subject receiving radiation or chemotherapy the composition of claim 1 thereby increasing the effectiveness of the radiation or chemotherapy.

10. A method for preventing, mitigating or treating colorectal neoplasia comprising administering to a subject in need thereof the composition of claim 1 so that the subject's colorectal neoplasia is prevented, mitigated or treated.

* * * * *